United States Patent
Chance

(10) Patent No.: US 9,980,960 B2
(45) Date of Patent: May 29, 2018

(54) METHODS FOR DETERMINING THE RISK OF CARDIOVASCULAR DISEASE IN A SUBJECT HAVING A CHRONIC VIRAL INFECTION

(71) Applicant: Case Western Reserve University, Cleveland, OH (US)

(72) Inventor: Mark R. Chance, Chagrin Falls, OH (US)

(73) Assignee: Case Western Reserve University, Cleveland, OH (US)

( * ) Notice: Subject to any disclaimer, the term of this patent is extended or adjusted under 35 U.S.C. 154(b) by 7 days.

(21) Appl. No.: 14/460,895

(22) Filed: Aug. 15, 2014

(65) Prior Publication Data

US 2016/0045494 A1 Feb. 18, 2016

(51) Int. Cl.

| | |
|---|---|
| *G01N 33/50* | (2006.01) |
| *G01N 33/53* | (2006.01) |
| *A61P 9/04* | (2006.01) |
| *A61P 9/10* | (2006.01) |
| *A61K 31/496* | (2006.01) |
| *G01N 33/573* | (2006.01) |
| *G01N 33/68* | (2006.01) |
| *C07K 14/47* | (2006.01) |
| *C12N 9/16* | (2006.01) |

(52) U.S. Cl.
CPC ............... *A61K 31/496* (2013.01); *A61P 9/04* (2018.01); *A61P 9/10* (2018.01); *G01N 33/50* (2013.01); *G01N 33/53* (2013.01); *G01N 33/573* (2013.01); *G01N 33/6893* (2013.01); *C07K 14/47* (2013.01); *C12N 9/16* (2013.01); *G01N 2333/916* (2013.01); *G01N 2405/04* (2013.01); *G01N 2800/32* (2013.01)

(58) Field of Classification Search
None
See application file for complete search history.

(56) References Cited

PUBLICATIONS

Schlatzer et al (2013. J Acquir Immune Defic Syndr. 63(5): 563-571.*
Adinolfi et al, 2012. Atherosclerosis. 221:496-502.*
Watanabe et al (2007. J Clin Gasteroenterol. 616-623).*
Quantikine ELISA Human ENPP-2/Autotaxin Immunoassay Product Data Sheet, Jun. 2013, 12 pages.*
Saga et al, 2014 (PLOS ONE. 9(4):e93230. 9 pages as printed).*

* cited by examiner

*Primary Examiner* — Zachary Howard
(74) *Attorney, Agent, or Firm* — Tarolli, Sundheim, Covell & Tummino LLP

(57) ABSTRACT

A method for determining the risk of cardiovascular disease in a subject having a chronic viral infection includes determining a level of ectonucleotide pyrophosphatase/phosphodiesterase-2 (ENPP2) in the subject and comparing the determined level of ENPP2 to a control level, wherein an increased level of ENPP2 is indicative of the subject having an increased risk of cardiovascular disease associated with the chronic viral infection.

4 Claims, 6 Drawing Sheets

Figs. 1A-D

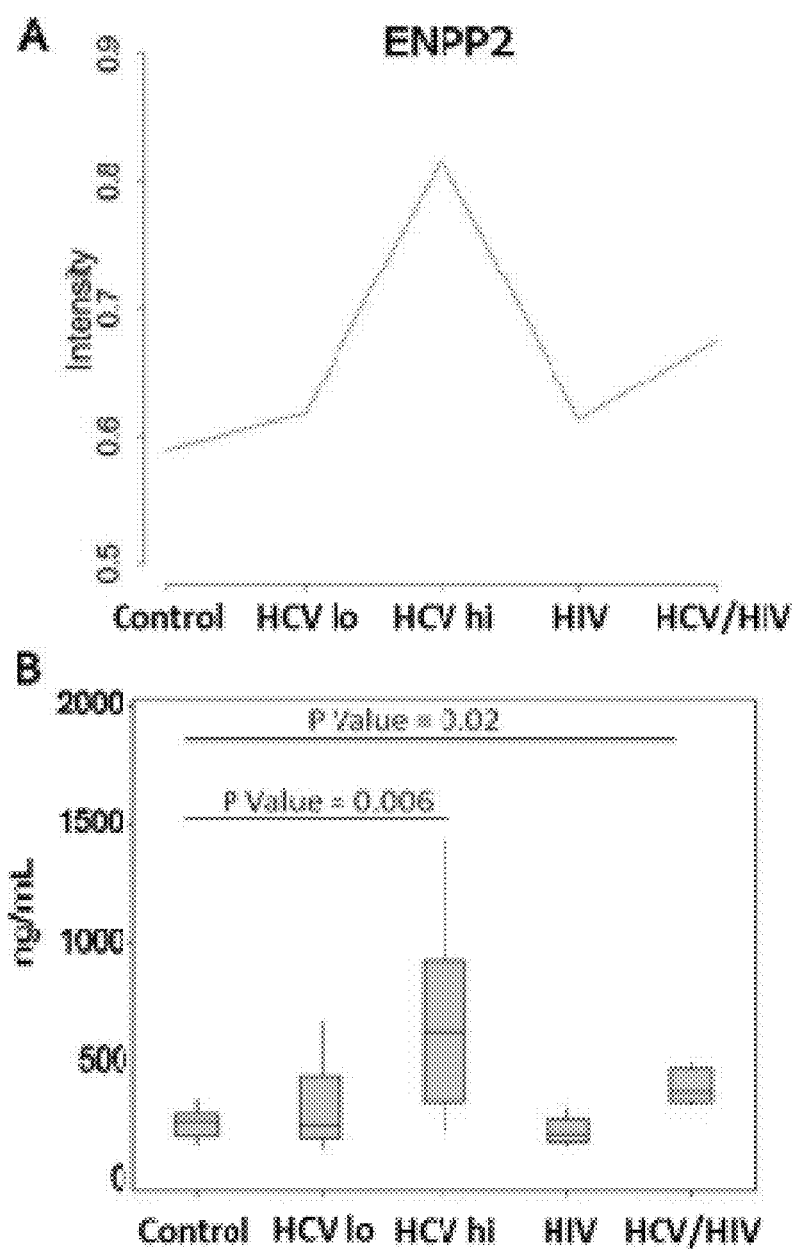
Figs. 3A-B

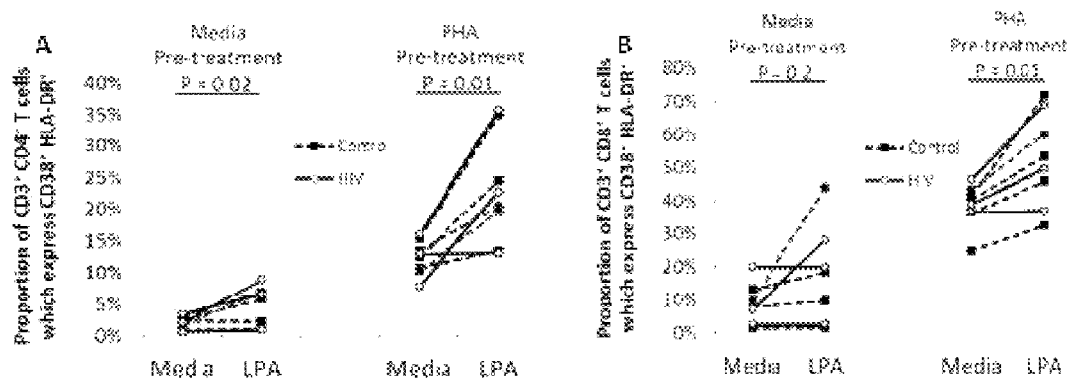
Figs. 4A-B
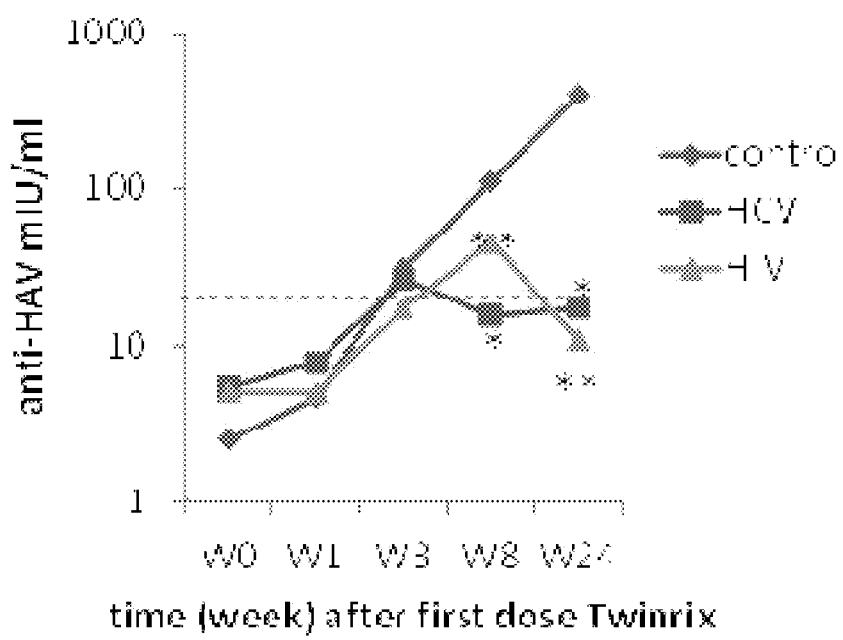
Fig. 5

Figs. 6A-D

METHODS FOR DETERMINING THE RISK OF CARDIOVASCULAR DISEASE IN A SUBJECT HAVING A CHRONIC VIRAL INFECTION

TECHNICAL FIELD

This application relates generally to methods and kits for determining the risk and/or severity of cardiovascular disease in a subject having a chronic viral infection and to methods for treating cardiovascular disease in a subject having an increased risk of cardiovascular disease resulting from a chronic viral infection.

BACKGROUND OF THE INVENTION

Due to overlapping modes of transmission, roughly 30% of HIV infected individuals are co-infected with HCV. While in recent years HIV related morbidity and mortality has been reduced with use of highly active antiretroviral therapy (HAART), HCV infection remains a cause of increased morbidity and mortality in HCV-HIV co-infected individuals as HIV has become a chronic condition. Though liver failure itself may account for a portion of this, HCV co-infection and liver disease are also associated with lower response to HBV vaccine, and greater cardiovascular disease, significant drivers of poor outcome during HIV infection.

Cardiovascular diseases have become of particular concern due to antiviral-drug-induced metabolic changes, the high prevalence of cardiovascular risk factors in HIV-infected individuals, and growing evidence on HIV-accelerated inflammatory processes that may promote atherosclerosis. In addition, HCV co-infection is associated with a higher prevalence of cardiovascular disease than HIV monoinfection. For example, HCV co-infection is associated with increased risk of cerebrovascular disease and a trend toward increased risk of acute myocardial infarction among HIV-infected patients.

Plasma proteins play a critical role in mediating inflammation and inate imuunity. Circulating levels of complement, defense collagens, and cytokines are essential in the immune response, playing roles such as modulation of antigen presentation and T/B-cell maturation/differentiation. Moreover, soluble innate immune molecules have emerged as important molecules in HIV and HCV pathogenesis. However, there remains a need to determine the functional significance of potential biomarkers of disease in the context of immune activation associated with disease progression in chronic viral infections.

SUMMARY OF THE INVENTION

An aspect of the application relates to a method for determining the risk of cardiovascular disease in a subject having a chronic viral infection. The method includes determining a level of ectonucleotide pyrophosphatase/phosphodiesterase-2 (ENPP2) in the subject. The method further includes comparing the determined level of ENPP2 to a control level, wherein an increased level of ENPP2 is indicative of the subject having an increased risk of cardiovascular disease associated with the chronic viral infection.

Another aspect of the application relates to a method for determining the risk of cardiovascular disease in a subject having a chronic viral infection. The method includes determining a level of lysophophatidic acid (LPA) in the subject. The method further includes comparing the determined level of ENPP2 to a control level, wherein an increased level of ENPP2 is indicative of the subject having an increased risk of cardiovascular disease associated with the chronic viral infection.

A further aspect of the application relates to a method for treating cardiovascular disease associated with chronic viral infection in a subject. The method includes administering a therapeutically effective amount of an ENPP2 inhibitor to the subject, the subject having increased levels of ENPP2 and/or LPA as compared to a control.

BRIEF DESCRIPTION OF THE DRAWINGS

The foregoing and other features of the present invention will become apparent to those skilled in the art to which the present invention relates upon reading the following description with reference to the accompanying drawings, in which:

FIGS. 3A-B are a series charts showing Peptide intensity based quantification of plasma proteome corresponds well with ELISA based determination of protein level. Panel A: intensity of individual peptides that correspond to ENPP2. Panel B: plasma protein level of ENPP2 across groups by ELISA. Again, HCV lo represents HCV infected subjects with the lowest APRI scores (<0.68) while HCV hi represents HCV infected subjects with the highest APRI scores (>0.68), where APRI is a marker of liver disease stage (higher APRI associated with more advanced liver disease stage).

FIGS. 4A-B are a series of charts showing LPA dependent T cell activation. 500,000 PBMC from 5 healthy controls and 3 untreated HIV infected subjects were cultured overnight in the absence or presence of PHA, followed by 3 days of culture in media or 100 uM LPA. Proportion of $CD3^+CD4^+$ (Panel A) and $CD3^+$ $CD8^+$ (Panel B) T cells that express of HLA DR and CD38 are shown. Statistical analysis shown for all 8 subjects combined. Comparisons between presence and absence of LPA in PHA pre-treated healthy control CD4 and CD8 activation were also significant (P=0.04, P=0.04).

FIG. 5 is a chart showing Hepatitis A antibody response to accelerated Twinrix immunization schedule is impaired during HCV and viremic HIV infection. Serum HAV specific IgG was measured by ELISA in viremic HIV infected subjects off HAART (n=24), chronic HCV infected (n=5), and healthy control (n=6) subjects receiving Twinrix at 0, 1, 3 week accelerated schedule. Geometric mean antibody levels are shown for each group as a function of time after first dose vaccine. Within HIV infected group 86% of subjects followed out to 24 weeks were HAV antibody positive at some point, while only 50% remained positive at 24 weeks. Within the control group 100% of subjects were antibody positive at week 24. Within the HCV infected group, 60% were positive at some point, while only 40% were positive at week 24. *=p<0.05 and **=p<0.001 compared to controls. Cutoff of 20 mIU/ml for positive result is shown (dotted line).

DETAILED DESCRIPTION

Figure 1:
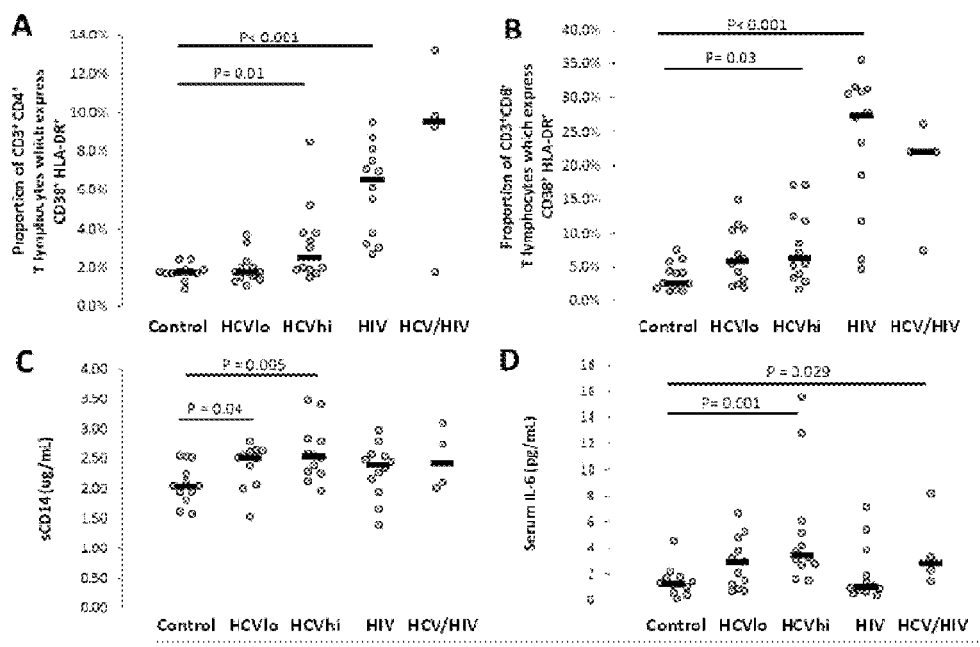
FIGS. 1A-D are a series of charts illustrating that immune activation is present during chronic HCV and HIV infections. Healthy control (n=12), chronic HCV infected with APRI<0.68 (HCVlo n=12), chronic HCV infected with APRI>0.68 (HCVhi n=12), untreated HIV infection (n=12), and HCV/HIV infected (n=4) subject PBMC and serum were analyzed by flow cytometry and ELISA. Panel A) Proportion of $CD3^+CD4^+$ T cells which are $CD38^+HLADR^+$. Panel B) Proportion of $CD3^+CD8^+$ T cells which are $CD38^+HLADR^+$. Panel C) Serum sCD14. Panel D) Serum IL-6. Statistically significant p values ($<0.05$) are shown for pair wise comparisons.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Ed., Springer-Verlag: New York, 1991, and Lewin, *Genes V*, Oxford University Press: New York, 1994. *The definitions provided herein are to facilitate understanding of certain terms used frequently herein and are not meant to limit the scope of the present invention.*

As used herein, the term "subject" can refer to any animal, including, but not limited to, humans and non-human animals (e.g., rodents, arthropods, insects, fish (e.g., zebrafish)), non-human primates, ovines, bovines, ruminants, lagomorphs, porcines, caprines, equines, canines, felines, ayes, etc.), which is to be the recipient of a particular treatment. Typically, the terms "patient" and "subject" are used interchangeably herein in reference to a human subject.

As used herein, the terms "cardiovascular disease," "cardiac disease," "cardiac disorder," "cardiovascular disorder," or "cardiovascular condition" can refer to any disease or disorder that negatively affects the cardiovascular system. The terms can also refer to cardiovascular events. "Cardiovascular events", as used herein, can include acute coronary syndrome, myocardial infarction, myocardial ischemia, chronic stable angina pectoris, unstable angina pectoris, angioplasty, stroke, transient ischemic attack, claudication(s) and vascular occlusion(s). In some aspects, cardiovascular diseases and disorders, therefore, can include acute coronary syndrome, myocardial infarction, myocardial ischemia, chronic stable angina pectoris, unstable angina pectoris, angioplasty, stroke, transient ischemic attack, claudication(s), vascular occlusion(s), arteriosclerosis, left ventricular dysfunction, heart failure, and cardiac hypertrophy.

As used herein, the term "pharmaceutically acceptable carrier" can include any material, which when combined with a conjugate retains the conjugate's activity and is non-reactive with a subject's immune system. Examples include, but are not limited to, any of the standard pharmaceutical carriers, such as a phosphate buffered saline solution, water, emulsions such as oil/water emulsion, and various types of wetting agents. Other carriers may also include sterile solutions, tablets including coated tablets, and capsules. Typically, such carriers contain excipients, such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

As used herein, the terms "administer" or "administering" can refer to oral administration, administration as a suppository, topical contact, intravenous, intraperitoneal, intramuscular, intralesional, intranasal or subcutaneous administration, or the implantation of a slow-release device e.g., a mini-osmotic pump to a subject. Administration can be by any route, including parenteral and transmucosal (e.g., oral, nasal, vaginal, rectal or transdermal). Parenteral administration can include, e.g., intravenous, intramuscular, intraarteriole, intradermal, subcutaneous, intraperitoneal, intraventricular, and intracranial. Other modes of delivery can include, but are not limited to, the use of liposomal formulations, intravenous infusion, transdermal patches, etc.

This application relates to methods for determining an increased risk and/or severity of cardiovascular disease in a subject having a chronic viral infection and to methods of treating cardiovascular disease in a subject having an increased risk of cardiovascular disease resulting from one or more chronic viral infections.

ENPP2 (ectonucleotide pyrophosphatase/phosphodiesterase-2), also known as autotoxin, or lysophospholipase-D is a key enzyme in the synthesis of the pro-inflammatory molecule lysophophatidic acid (LPA). Downstream effects of LPA include immune activation, neuropathic pain modulation, platelet aggregation, wound healing, vasopressor activity, atherosclerosis and angiogenesis.

Using an unbiased proteomic analysis it was found that both plasma LPA and ENPP2 levels and activity are increased in subjects having a chronic viral infection, and that this increase is correlated with CD4+ T cell activation. In addition, it was found that plasma LPA and ENPP2 levels and activity are correlated with established markers of chronic immune activation (CIA), (i.e., HLA-DR and CD38 expression on CD4 and CD9 T-cells, sCD14, and IL-6). Moreover, the plasma LPA and ENPP2 levels were correlated to disease state and the severity of immune activation and infection outcome in subjects having a chronic viral infection. Higher ENPP2, levels and therefore LPA can be indicative of clinical outcome during HIV, HCV and HCV-HIV co-infections. For example, it was shown that plasma ENPP2 is especially elevated during hepatitis C virus (HCV) infection in subjects exhibiting the most severe forms of CIA.

Therefore, it is believed that the ENPP2/LPA inflammatory pathway is the mediator for chronic immune activation (CIA) and subsequent morbidity and mortality related to chronic viral infections. Without being bound by theory, it is believed that chronic viral infections, such as HCV, induce expression of ENPP2 that in turn drives increased LPA levels, which activates naïve and memory T cells as well as monocytes, NK and B cells (either directly from LPA-dependent signaling or indirectly via LPA-activated T cells) resulting in chronic vascular inflammation and subsequent cardiovascular disease.

Based on these discoveries, it was determined that subjects, which have an increased level of ENPP2 and/or LPA compared to control subjects, have increased risk of cardiovascular disease and that ENPP2 and/or LPA can be measured in a subject to determine or predict if the subject has increased risk of cardiovascular disease associated with a chronic viral infection.

Accordingly, an aspect of the application relates to a method for determining the risk of cardiovascular disease in a subject having a chronic viral infection. The method includes determining the level of ENPP2 and/or LPA in the subject.

The level of ENPP2 and/or LPA can be determined by first obtaining one or more biological samples from a subject. In one example, the levels of the ENPP2 and LPA can both be determined by first obtaining a single biological sample from a subject. In another example, the levels of ENPP2 and LPA can each be determined separately by obtaining two or more biological samples from a subject.

The subject can be a subject known to have or suspected of having a chronic viral infection. In some aspects, the subject can have an HIV, HCV or HIV-HCV co-infection. Subject having a chronic viral infection (e.g., >6 mos) may be determined using methods well known in the art such as PCR, Western Blot and ELISA based assays. Subjects include those who have and who have not received antiretroviral treatment prior to the biological sample being obtained. In particular aspects, subjects can include chronic HCV infected (untreated), chronic HIV infected, and chronic HCV-HIV infected subjects virally suppressed on HAART.

Subjects at risk for a cardiovascular disease related to a chronic viral infection can exhibit any one or combination of additional risk factors for cardiovascular disease including, but not limited to, elevated blood pressure, an abnormal response to a stress test, elevated levels of myeloperoxidase, C-reactive protein, low density lipoprotein, cholesterol, or atherosclerotic plaque burden. Techniques for assessing cardiovascular disease risk factors are known in the art and can include coronary angiography, coronary intravascular ultrasound, stress testing (with and without imaging), assessment of carotid intimal medial thickening, carotid ultrasound studies with or without implementation of techniques of virtual histology, coronary artery electron beam computer tomography, cardiac computerized tomography (CT) scan, CT angiography, cardiac magnetic resonance imaging, and magnetic resonance angiography.

The biological sample including ENPP2 and/or LPA can include whole blood samples and samples of blood fractions, such as serum and plasma. The biological sample may be fresh blood, stored blood (e.g., in a blood bank), or a blood fraction. The biological sample may be a blood sample expressly obtained for the assay(s) described herein or, alternatively, a blood sample obtained for another purpose which can be sub-sampled. In one example, the biological sample can comprise whole blood. Whole blood may be obtained from the subject using standard clinical procedures. In another example, the biological sample can comprise plasma. Plasma may be obtained from whole blood samples by centrifugation of anti-coagulated blood. Such process provides a buffy coat of white cell components and a supernatant of the plasma. In yet another example, the biological sample can comprise serum. Serum may be obtained by centrifugation of whole blood samples that have been collected in tubes that are free of anti-coagulant. The blood may then be permitted to clot prior to centrifugation. The yellowish-reddish fluid obtained by centrifugation is the serum. In one example, a biological sample including ENPP2 and/or LPA can include blood serum or plasma.

Biological samples can be pretreated as necessary by dilution in an appropriate buffer solution, heparinized, concentrated if desired, or fractionated by any number of methods including, but not limited to, ultracentrifugation, fractionation by fast performance liquid chromatography, precipitation with dextran sulfate, or other known methods. Any number of standard aqueous buffer solutions employing one or a combination of buffers, such as phosphate, Tris, or the like, at physiological pH can also be used.

After obtaining the biological sample from the subject, the level of the pro-inflammatory pathway molecule ENPP2 and/or LPA is determined using any one or combination of known biochemical assays or techniques. Examples of biochemical assays or techniques that can be used to determine the level of ENPP2 and/or LPA include, for example, antibody based assays, such as ELISA and Western blots, mass spectroscopy (MS) (e.g., LC/ESI/MS/MS), fluorometric assays and chromatography (e.g., HPLC, affinity column, etc.). In one aspect, the plasma concentration level of ENPP2 can be determined using an ELISA assay.

Once the levels of ENPP2 and/or LPA have been determined, the level of ENPP2 and/or LPA is compared to control levels in order to determine an increased risk of cardiovascular disease associated with chronic viral infection in the subject. For example, the level of ENPP2 in a biological sample can be determined using ELISA and then the level can be compared to a control level or value of ENPP2. The control levels can be based upon the level of ENPP2 in a comparable biological sample (or samples) obtained from a control population (e.g., the general population) or a select population of subjects. For example, the select population may be comprised of apparently healthy subjects, subjects determined to have cardiovascular disease associated with a chronic viral infection, and/or subjects determined to have little or no cardiovascular disease resulting from chronic viral infection. In certain aspects, controls populations can include populations having untreated chronic HCV infection (subdivided in to low (HClo) and high (HCVhi) AST/Platelet ration index (APRI)), untreated HIV infection, untreated HCV-HIV co-infection, chronic HCV-HIV infection suppressed by HAART.

The control levels can be related to the levels used to characterize the levels of the ENPP2 and/or LPA obtained from the subject. For example, if the level of the ENPP2 is an absolute value, such as the units of ENPP2 per ml of blood, the control level can also based upon the units of ENPP2 per ml of blood in subjects of the general population or a select population. Similarly, if the level of ENPP2 and/or LPA is a representative value, such as an arbitrary unit obtained from an ELISA, the control level can also be based on the representative value.

The control levels can also take a variety of forms. For example, the control levels can be a single cut-off value, such as a median or mean. The control levels can be established based upon comparative groups, such as where the risk in one defined group is double the risk of another defined group. The control levels can also be divided equally (or unequally) into groups, such as a low-risk group, a medium-risk group, and a high-risk group, or into quadrants, the lowest quadrant being subjects with the lowest risk the highest quadrant being subjects with the highest risk.

Control levels of ENPP2 and/or LPA in biological samples, for example, can be obtained (e.g., mean levels, median levels, or "cut-off" levels) by assaying a large sample of subjects in the general population or a select population and then using a statistical model, such as the predictive value method for selecting a positivity criterion or receiver operator characteristic curve that defines optimum specificity (highest true negative rate) and sensitivity (highest true positive rate), as described in Knapp, R. G. and Miller, M. C. (1992): *Clinical Epidemiology and Biostatistics*, William and Wilkins, Harual Publishing Co. (Malvern, Pa.), which is incorporated herein by reference.

Depending upon the levels or values of ENPP2 and/or LPA when compared to the control levels, a determination can be made as to the risk of cardiovascular disease associated with a chronic viral infection in the subject. In an example of the method, an increased level of ENPP2 and/or LPA as compared to control value levels may indicate an increased risk of developing cardiovascular disease associated with a chronic viral infection mediated by CIA or in some cases even a more severe form of a cardiovascular disease. Thus, a subject with an increased level of ENPP2 and/or LPA may have an increased risk of having a myocardial infarction as compared to a control subject. Alternatively, a normal or reduced level of ENPP2 and/or LPA as compared to a control value level may indicate little or no risk of a subject having a myocardial infarction or other cardiovascular disease or disorder associated with a chronic viral infection.

In another aspect of the application, a kit is provided for determining the risk of cardiovascular disease in a subject having a chronic viral infection. The kit includes at least one first reagent that specifically detects and/or determines the level of ENPP2 and/or LPA, such as an ENPP2 and/or LPA polypeptide, an ENPP2 and/or LPA polypeptide fragment, a polynucleotide encoding an ENPP2 and/or LPA polypeptide, or a polynucleotide encoding a fragment of an ENPP2 and/or LPA polypeptide in a subject, and instructions for using the kit to determine an increased risk of cardiovascular disease in a subject diagnosed with or suspected of having a chronic viral infection.

In an example of the application, a first reagent can detect expression levels of an ENPP2 polypeptide or fragment thereof via an antibody that specifically binds to the ENPP2 polypeptide or fragment thereof. In other example, the first reagent can comprises a nucleic acid probe complementary to a polynucleotide sequence coding for an ENPP2 polypeptide or fragment thereof. For example, the nucleic acid probe may be a cDNA or an oligonucleotide immobilized on a substrate surface.

The instructions of the kit can include instructions required by a regulatory agency (e.g., the U.S. Food and Drug Administration) for use in in vitro diagnostic products. For example, the instructions can be applicable to one or more of an extraction buffer/reagent(s) and a related protocol, an amplification buffer/reagent(s) and a related protocol, a hybridization buffer/reagent(s) and a related protocol, an immunodetection buffer/reagent(s) and a related protocol, a labeling buffer/reagent(s) and a related protocol, and/or a control value or values (as described above).

It is further contemplated that the sustained induction of ENPP2 and its pro-inflammatory lipid mediator LPA resulting in the exacerbation of cardiovascular disease in a subject having a chronic viral infection can be reversed or prevented with the use of an ENPP2 inhibiting agent. Therefore, another aspect of the invention relates to therapies which selectively interrupt persistent viral infection-mediated CIA to reduce long term morbidity and mortality by improving cardiovascular health in subjects having a chronic viral infection.

Accordingly, this application provides a method for treating cardiovascular disease in a subject having an increased risk of increased risk of cardiovascular disease associated with a chronic viral infection. The method includes administering therapeutically effective amounts of an ENPP2 inhibitor to the subject. In one example, the subject is determined to have an increased risk of a cardiovascular disease associated with HIV, HCV, or HIV/HCV co-infection as described herein.

A variety of suitable ENPP2 inhibitors can be used with the methods of the invention. Examples include a chemical compound or an antibody that specifically binds the ENPP2 or an ENPP2 binding fragment thereof such as a single-chain antibody (e.g., humanized). Other examples include a synthetic ENPP2 substrate, ENPP2 product analog, or a natural inhibitor. A particular example of an ENPP2 product analog is Brp-LPA. In some aspects the ENPP2 inhibitor is selected from PF8380, S 32826, HA 130, and ONO-8430506. In certain aspects the ENPP2 inhibitor is PF8380.

As used herein, the term "therapeutically effective amounts" can refer to the amount of an ENPP2 inhibitor administered to a subject that results in lowering or eliminating the risk cardiovascular disease in a subject found to have an increased risk of cardiovascular disease associated with a chronic viral infection. A therapeutically effective amount can also refer to a prophylactically effective amount. As used herein, a "prophylactically effective amount" is an amount of an ENPP2 inhibitor that, when administered to a subject, will have the intended prophylactic effect, e.g., preventing or delaying the onset (or reoccurrence) of cardiovascular disease or symptoms, or reducing the likelihood of the onset (or reoccurrence) of cardiovascular disease or symptoms. The full prophylactic effect does not necessarily occur by administration of one dose and may occur only after administration of a series of doses. Thus, a prophylactically effective amount may be administered in one or more administrations. In one example, about 30 mg/kg, twice daily, of the ENPP2 inhibitor PF-8380 (PFIZER) can be administered to a subject.

In some aspects, the therapeutic effectiveness of an ENPP2 inhibitor administered to a subject in need thereof can be determined by assessing T cell activity and viremia in a subject as these are the two most critical physiological endpoints in humans for effective anti-viral immunity versus dysfunctional CIA.

The therapeutically effective amounts an ENPP2 inhibitor can be administered in an isolated or concentrated form, or as a part of one or more pharmaceutical compositions and/or formulations. In one embodiment, a pharmaceutical composition can include ENPP2 inhibitor as the active ingredient and a pharmaceutically acceptable carrier or aqueous medium excipient suitable for administration and delivery in vivo. Combined therapeutics are also contemplated, and the same type of underlying pharmaceutical compositions may be employed for both single and combined medicaments. For example, a pharmaceutical composition described herein can include two or more ENPP2 inhibitory agents described above as the active ingredients and a pharmaceutically acceptable excipient suitable for administration and delivery in vivo.

A pharmaceutical composition described herein can be administered by any appropriate route, such as percutaneous, parenteral, subcutaneous, intravenous, intraarticular, intrathecal, intramuscular, intraperitoneal, or intradermal injections, or by transdermal, buccal, oromucosal, ocular routes, or via inhalation. The dosage administered will be dependent upon the age, health, and weight of the subject, kind of concurrent treatment, if any, frequency of treatment, and the nature of the effect desired. In a subject with an increased level of ENPP2 and/or LPA for example, a therapeutically effective amount of a pharmaceutical composition comprising an ENPP2 inhibitor can be prophylactically administered to prevent or mitigate a cardiovascular disease or disorder.

In addition to one or more active ingredients (e.g., an ENPP2 inhibitor), pharmaceutical compositions can include pharmaceutically acceptable carriers comprising excipients and auxiliaries that facilitate processing of an active ingredients into pharmaceutical preparations. The pharmaceutical preparations of the present invention can be manufactured in a known manner by, for example, means of conventional mixing, granulating, dragee-making, dissolving, or lyophilizing processes. Thus, pharmaceutical preparations for oral use can be obtained by combining the active agents with solid excipients, optionally grinding the resulting mixture, and processing the mixture of granules after adding suitable auxiliaries, if desired or necessary, to obtain tablets or dragee cores.

Suitable excipients can include fillers, such as saccharides (e.g., lactose or sucrose, mannitol or sorbitol), cellulose preparations and/or calcium phosphates (e.g., tricalcium phosphate or calcium hydrogen phosphate), as well as binders, such as starch paste using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as the above-mentioned starches, as well as carboxymethylstarch, cross-linked polyvinyl pyrrolidone, agar, or alginic acid or a salt thereof, such as sodium alginate. Auxiliaries are flow-regulating agents and lubricants, for example, silica, talc, stearic acid or salts thereof, such as magnesium stearate, or calcium stearate, and/or polyethylene glycol. Dragee cores can be provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions, and suitable organic solvents or solvent mixtures.

To produce coatings resistant to gastric juices, solutions of suitable cellulose preparations, such as acetylcellulose phthalate or hydroxypropylmethylcellulose phthalate can be used. Slow-release and prolonged-release formulations may be used with particular excipients, such as methacrylic acid-ethylacrylate copolymers, methacrylic acid-ethyl acrylate copolymers, methacrylic acid-methyl methacrylate copolymers, and methacrylic acid-methyl methylacrylate copolymers. Dye stuffs or pigments can be added to the tablets or dragee coatings, for example, for identification to characterize combinations of active compound doses.

Other pharmaceutical preparations that can be used orally include push-fit capsules made of gelatin, as well as soft, sealed capsules made of gelatin and a plasticizer, such as glycerol or sorbitol. The push-fit capsules can contain the active compounds in the form of granules that may be mixed with fillers, such as lactose, binders, such as starches, and/or lubricants, such as talc or magnesium stearate and, optionally, stabilizers. In soft capsules, one or more active ingredients (e.g., ENPP2 inhibitor) can be dissolved or suspended in suitable liquids, such as fatty oils or liquid paraffin.

Examples of formulations for parenteral administration can include aqueous solutions of one or more active ingredients in water-soluble form, for example, water-soluble salts, and alkaline solutions. Examples of salts can include maleate, fumarate, succinate, S,S tartrate, or R,R tartrate. In addition, suspensions of one or more of the active ingredients as oily injection suspensions can be administered. Suitable lipophilic solvents or vehicles include fatty oils, for example, sesame oil, or synthetic fatty acid esters, for example, ethyl oleate or triglycerides or polyethylene glycol-400. Aqueous injection suspensions can contain substances that increase the viscosity of the suspension, sodium carboxymethyl cellulose, sorbitol, and/or dextran.

The therapeutically effective amounts of the ENPP2 inhibitor can be administered to a subject on a desired dosing schedule. For example, a therapeutically effective amount of a pharmaceutical composition comprising an ENPP2 inhibitor can be administered about four times daily, about three times daily, about twice daily, about daily, about every other day, about three times weekly, about twice weekly, about weekly, about every two weeks, or less often (as desired). In one example, a therapeutically effective amount of a pharmaceutical composition includes 30 mg/kg of the ENPP2 inhibitor PF-8380 and is administered to the subject twice daily.

A therapeutically effective amount of an ENPP2 inhibitor can also be administered for a duration sufficient to provide a prophylactic effect. For example, a therapeutically effective amount of ENPP2 inhibitor can be administered daily for one year, for about six months, about a year, about two years, about five years, about 10 years, or indefinitely. It will be apparent to those of skill in the art that the dose, dosing schedule, and duration can be adjusted for the needs of a particular subject, taking into consideration the subject's age, weight, type of viral infection, severity of cardiovascular disease, and other co-morbid conditions.

Toxicity and therapeutic efficacy of compositions comprising an ENPP2 inhibitor for use in the invention can be determined using standard pharmaceutical procedures in cell culture or experimental animals for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50.

The following example is for the purpose of illustration only and is not intended to limit the scope of the claims, which are appended hereto.

Example 1

Effect of ENPP2 on Chronic Immune Activation and HCV, HIV and LCMV Infection

Morbidity and mortality during HIV infection is commonly attributable to cardiovascular disease and Hepatitis C virus (HCV) co-infection. HCV-HIV co-infection is associated with lower response to vaccines (e.g. HAV and HBV) and greater cardiovascular morbidity than HIV mono-infection. We and others have reasoned that chronic immune activation (denoted "CIA" heretofore) is a potential cause for both immune dysfunction (exhaustion and impaired memory and neoantigen response) and cardiovascular disease. CIA is reflected by soluble markers, such as plasma IL-6 and sCD14, as well as cellular markers such as T-cell HLA-DR and CD38 expression. These markers are predictive of disease progression during HIV infection, and evidence supports the same for HCV and HCV-HIV co-infection. We hypothesize that therapies which selectively interrupt persistent viral infection-mediated CIA will reduce long term morbidity and mortality by improving cardiovascular health and immune response to pathogen and vaccine challenge in the setting of HCV-HIV infection. To identify molecular drivers of CIA, we performed a non-biased comprehensive plasma proteome analysis to determine correlates of CIA during HCV, HIV and HCV-HIV infection. Our lead molecule was plasma ENPP2 (autotaxin). ENPP2 was elevated during HCV infection with advanced liver disease (cohort exhibiting the most severe CIA), and best correlated with CD4 T cell activation during HCV and HIV infection. The product of ENPP2 activity, lysophosphatidic acid (LPA), activates T cells, providing a potential mediator of CIA, and thus a potential target for therapeutic intervention.

We will determine the effect of HCV infection on in vivo ENPP2 levels in subjects undergoing anti-HCV treatment, the therapeutic potential of removing LPA to restore exhausted T cell activity in vitro, and explore the relationship between in vivo ENPP2/LPA and response to neoantigen during chronic HCV and HIV infection. LPA directly and indirectly activates T cells, monocytes, B cells and NK cells, in turn resulting in impaired response to neoantigen vaccine. Removal of HCV from an individual is hypothesized to only partially normalize CIA, ENPP2 and LPA levels, while removal of LPA from the system will better restore cellular immune function. We will determine whether accessory cells are required for in vitro LPA induced T cell activation and additional defined markers of CIA (monocyte and B cell activation and related sCD14 and IL-6 production). We will determine whether T cell response to neoantigen vs. recall antigen can be restored after removal of LPA in in vitro culture. We will determine whether ENPP2 levels and other markers of CIA normalize after removal of HCV from the human host using standard HCV treatment. We will determine whether higher ENPP2 level negatively predicts response to neoantigen vaccine during HCV and/or HIV infection.

We will determine the effect of ENPP2 inhibition on murine host response to neoantigen in the setting of chronic LCMV infection. While an adequate model of chronic HCV infection containing the virus itself in the context of an intact immune system does not currently exist, LCMV is the prototypical and best characterized model for chronic viral infection. Features shared between HCV, HIV and LCMV infection include CIA, exhaustion, naïve CD4 lymphopenia, and ENPP2 elevation (preliminary data). To directly address the functional relevance of ENPP2 pharmacologic inhibition in a preclinical physiologically relevant model system, we will use the chronic LCMV infection model. We will test our hypothesis that ENPP2 impairs response to neoantigen by comparing chronic LCMV infected host response to immunization in the presence vs. absence of ENPP2 inhibition. We will also determine the effect of ENPP2 inhibition on LCMV infection itself.

ENPP2 and LPA are known to be pro-inflammatory molecules increased in the setting of chronic HCV infection with advanced liver disease. Our newly appreciated linkage between ENPP2 and plasma/cellular markers of immune activation provides a new and novel focus on mechanisms underlying CIA. Identification of therapeutic targets in humans is essential. In order to clinically translate these approaches, evaluation of the effect of pathway interruption using small molecule inhibitors that may be used in humans, using an appropriate animal model system, provides maximal insight. The outcome of the proposed studies will: A) identify interactions between ENPP2, LPA, HCV, HIV, LCMV and the immune system; and B) evaluate the physiological effects on both host and virus when interrupting a therapeutic target in pre-clinical models.

We and others have observed systemic CIA (CD4+CD38+ HLADR+, CD8+CD38+HLADR+, sCD14, IL-6, B cell subset skewing, NK subset skewing, DC subset activation and skewing, naïve CD4 cell lymphopenia and increased cell cycling) in the setting of chronic HCV infection. Immune activation positively correlates with liver disease stage, and negatively predicts IFN based HCV therapy response during HCV monoinfection and HCV-HIV coinfection. ENPP2 (ectonucleotide pyrophosphatase/phosphodiesterase-2) is also known as autotaxin, or lysophospholipase-D. It is a key enzyme in lysophosphatidic acid (LPA) synthesis. Downstream effects of LPA include immune activation, neuropathic pain modulation, platelet aggregation, wound healing, vasopressor activity, atherosclerosis and angiogenesis. Both plasma LPA and ENPP2 levels and activity are increased in chronic HCV infection, correlated with each other, and associated with disease stage. LPA also regulates stellate cell proliferation, though it is unclear if it is a cause or effect of liver injury. Finally, ENPP2 mRNA is overexpressed within the liver of HCV infected subjects with HCC compared to those without. Since LPA activates T cells, elevated ENPP2 and LPA levels during HCV infection may in fact directly contribute to CIA. Model: We propose HCV and associated liver disease induces expression of ENPP2 that in turn drives increased LPA levels, which activates naïve and memory T cells as well as monocytes, NK and B cells (either directly from LPA-dependent signaling or indirectly via LPA-activated T cells). This results in impaired response to neoantigen and vaccine, as well as chronic vascular inflammation.

Plasma proteome analysis reveals plasma proteins that are associated with CIA during HCV and HIV infection. To gain insight into markers and mediators of immune activation in HCV and HIV infection we conducted unbiased plasma proteomic profiling, where hundreds of proteins were quantified. We studied persons with untreated chronic HCV infection (subdivided into low (HCVlo) and high (HCVhi) AST/Platelet ratio index (APRI, where higher APRI is associated with more advanced liver disease stage) subgroups, untreated HIV infection, HCV-HIV co-infection and healthy controls. As expected, proportions of CD4 and CD8

T-cells that express HLADR and CD38 were greater in HIV and HCVhi groups compared to controls (FIGS. 1A and 1B). Soluble CD14 level was greater in both HCV infected groups than controls (1C), and serum IL-6 levels were greater in HCVhi and HCV-HIV subject groups than among controls (1D). These findings are consistent with previous literature and provide a comparative view of immune activation in HCV vs. HIV infection. Plasma proteome analysis identified 2,297 peptides mapping to 227 proteins. Of those, 360 peptides mapping to 85 proteins differed across groups (FDR<0.10). We next assessed whether established markers of immune activation (HLA-DR and CD38 expression on CD4 and CD8 T-cells, sCD14, and IL-6) correlated with plasma protein abundance for proteins that differed in abundance among groups. Peptide intensities mapping to 43 proteins significantly correlated (p<0.05) with a parameter of immune activation within one or more disease group. We focused on proteins capable of immune modulatory function. Two proteins were identified in this way. We focused attention on ENPP2. It correlated with activated CD4 T-cell frequencies in both HCV and HIV groups (FIG. 2), and with sCD14 and IL-6 in the HCV infected groups (p<0.05 each). Plasma concentration of ENPP2 was verified by ELISA (FIG. 3), and was found to be greater in HCV high APRI and HCV-HIV infected groups.

To determine whether LPA can directly contribute to immune activation we have conducted LPA induced T cell activation assays using HLADR and CD38 co-expression as a readout (FIG. 4). As shown, LPA enhanced T cell activation over a 4 day culture. Activation was observed in the CD4 compartment regardless of pre-activation, though the effect was more robust in the presence of pre-activation with PHA. These data provide proof of concept that LPA can contribute to T cell activation, either directly or through accessory cells.

Figure 6:
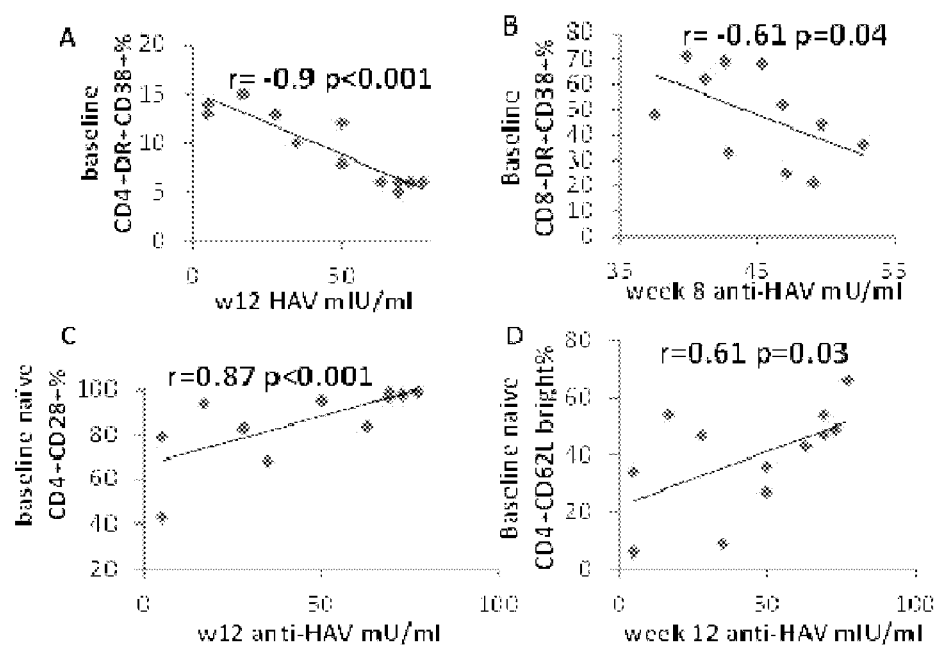
FIGS. 6A-D are a series of charts showing baseline CD4 and CD8 cell immune activation negatively correlates with HIV host response to HAV vaccine, while baseline naïve CD4 frequency and proportions of naïve CD4 cells expressing CD28 positively correlate with vaccine response. Panel A: week 12 serum anti-HAV mU/ml vs. baseline CD4 activation. Panel B: week 8 serum anti-HAV vs. baseline CD8 activation. Panel C: week 12 anti-HAV vs. baseline proportion of naïve CD4 (CD45RO-CD62L+) expressing CD28. Panel D: week 12 anti-HAV vs. baseline frequency of CD62L bright naïve CD4 cells.

AIDS Clinical Trials Group (ACTG) A5232 is a study evaluating immune predictors of response to neoantigen. We have extended this study to include healthy control and HCV mono-infected arms (Case/UHC, Metro, U Cincinnati). Hep A/Hep B naïve subjects were immunized with Twinrix (accelerated 0, 1, 3 week dosing) and tetanus vaccines. Though we have only partially evaluated these data (n=24 HIV, 5 HCV, 6 controls), the week 8 anti-HAV response is lower in both HCV and HIV infected groups compared to controls (FIG. 5). While 100% of control subjects responded at 24 weeks, <50% of the HCV and HIV subjects responded. We evaluated whether parameters of immune activation, i.e., T cell activation at baseline, are predictive of response (Hepatitis A antibody) in the HIV group. We observed higher frequencies of activated CD4 and CD8 cells to negatively predict week 8 and 12 anti-HAV level, while proportions of naïve CD4 cells, and T cells that express CD28 positively predict week 12 HAV titer (FIG. 6). Additionally, a more stringent definition for naïve CD4 Cells (CD62L bright) demonstrated a positive correlation between naïve CD4 cell frequency itself and response to neoantigen vaccine. We will determine if these relationships extend to HBV vaccine or tetanus response, extend to chronic HCV and HIV-HCV infection, or are associated with ENPP2 as described below.

Figure 7:
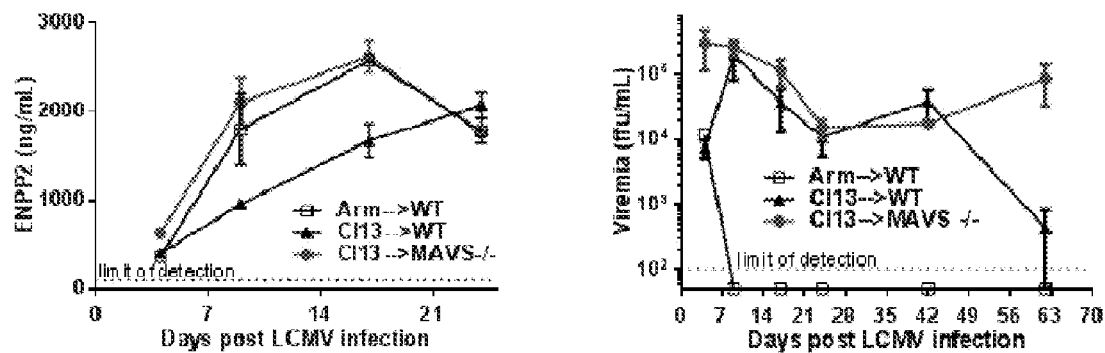
FIG. 7 illustrates differential induction of ENPP2 during persistent viral infection dependent on cytoplasmic sensor MAVS. WT and MAVS−/− mice were infected with $2\times10^6$ pfu LCMV Armstrong (Arm) or Clone 13 (Cl13) to establish acute and persistent infections, respectively. Mean and SEM of serum ENPP2 levels by ELISA (left) and viremia (right) are plotted on the Y-axis as shown. 3-4 mice/group.

We have tested key targets applicable to HCV and HIV infection using the mouse LCMV model. As part of this collaboration we investigated ENPP2 level during LCMV infection. We observed delayed and extended induction of ENPP2 in chronic (clone 13) versus acute (ARM) viral infections (FIG. 7). This differential induction was MAVS (innate sensor for both HCV and LCMV) dependent. This indicates conservation between HCV and LCMV in regard in the host immune response, and highlights the readily available infrastructure for functional interrogation of the role of ENPP2 in host immunity to neoantigen using the LCMV model.

We will determine the effect of HCV infection on in vivo ENPP2 levels in subjects undergoing anti-HCV treatment, the therapeutic potential of removing LPA to restore exhausted T cell activity in vitro, and explore the relationship between in vivo ENPP2/LPA and response to neoantigen during chronic HCV and HIV infection. LPA activates T cells and monocytes. Specific focus on CIA parameters (IL-6, sCD14, HLA DR and CD38 co-expression on T cells) associated with HCV and HIV disease stage and progression has not been evaluated. We will further determine whether accessory cells are required for LPA induced T cell activation and extend in vitro assays to focus on monocyte and B cell activation and IL-6 producing activity. We will determine whether T cell response to neoantigen vs. recall antigen can be restored after removal of LPA in ex vivo culture. Both HCV infection and liver damage are drivers of ENPP2 and LPA levels. The discrete contribution of each of these factors is unclear. Our preliminary data with LCMV in mice (FIG. 7) suggest that ENPP2 and LPA levels may normalize after removal of virus from the host. We will directly address this in subjects by comparing ENPP2, LPA and other immune activation markers pre and post anti-HCV treatment. CIA correlates with immune dysfunction. Our preliminary data demonstrate CD4 T cell activation negatively predicts HIV infected host responses to HAV neoantigen vaccine, while naïve CD4 cell frequency positively predicts response. Like HIV, chronic HCV infection is associated with naïve CD4 lymphopenia. We propose our preliminary HIV observations will extend to HCV and HCV-HIV infection. We will determine whether ENPP2 and/or LPA levels predict response to neoantigen vaccine during HCV and/or HIV infection.

Samples:

We will use freshly prepared samples from healthy control, chronic HCV infected (untreated), chronic HIV infected, and chronic HCV-HIV infected subjects virally suppressed on HAART. Initial experiments will be performed with 5 subjects/group, then repeated twice to verify. HCV infected subjects will be selected to span the spectrum of HCV disease stage (APRI score and biopsy score) in the initial experiment, then in subsequent experiments we will stratify enrollment by disease stage (APRI and biopsy). HCV infected subjects will have chronic HCV infection (>6 months), and not have received therapy for HCV infection. HIV infected subjects will have HIV infection (prior HIV PCR+, Western and ELISA+), and <50 HIV copies/ml on HAART. For Sub Aim B subjects will have received HBV/HAV vaccine within the past year. Sub Aim C will be performed on cryopreserved samples from 15 subjects/group in the following longitudinally sampled groups: 1) chronic HCV infection with low APRI (<1) (biopsy information available), plasma sample A prior to therapy and sample B after sustained response to HCV therapy (6 months after completion of therapy and virus negative at that time point); 2) chronic HCV infection with high APRI (>1) (biopsy available), sample A prior to therapy and sample B after sustained response to HCV therapy. Based on our preliminary data showing elevated ENPP2 plasma level in HCV high APRI subjects using a sample size of 12/group, a sample size of 15/group with paired samples should more than suffice. Sub Aim D: we will utilize cryopreserved samples from our ongoing A5232 and CFAR0910 studies where subjects were administered twinrix and tetanus vaccine. This is an exploratory subaim so we will use all available healthy control (n=10), HCV (n=15), HIV (n=22) and HCV/HIV (n=4) infected subject samples prior to immunization.

Assay Plan: Accessory cell help and soluble factor requirement and cellular activation assays. Sub Aim A: Initial assays will address isolated cell sufficiency for activity and will be performed with negatively selected bead purified bulk CD4 and CD8 cells, evaluating LPA induced HLADR and CD38 expression as outlined in FIG. 4, performed in the presence and absence of PHA pre-activation. The pre-activation likely requires APC, so we will also perform pre-activation cultures with agonistic anti-CD3 and -CD28 antibodies. Additionally, we will measure T cell proliferation by CFSE dye dilution, and T cell IL-2 production by flow cytometry. Monocyte, DC and B cell targeted assays will be performed in parallel (negative bead selection of bulk cell populations as well as unfractionated PBMC assays), scoring for CD80/86 expression by flow cytometry, and monocyte/B cell/DC cytokine (IL-6, TNF-α, IL-10, IL-1, IL-12) secretion (with purified cells) vs. intracellular cytokine analysis by flow cytometry (with unfractionated cells). Once it is determined that there is incomplete sufficiency in activity with purified cell populations we will perform supernatant transfer assays. If soluble factor facilitates activity we will carry assays forward with trans-well method, purified accessory cell co-culture assays, and selective targeting of known soluble factors governing cell-cell interactions (IL-12, TNFα, IL10, IL-1, IL-6). Cell contact factors such as CD40L would also be investigated.

Sub Aim B: Antigen specific T cell assays, and ENPP2, PD1 and Tim3 blockade. HCV genotype 1a peptide pools (10 pools of peptides) will be utilized at 2.7 µg/ml each peptide as we have previously described, and recombinant tetanus, HBV and HAV antigen will be utilized at 10 µg/ml. We will perform antigen specific (HCV peptide pool chosen based upon which peptide pool targeted in each individual using overnight ELISPOT assay first, HBsAg, HAV, tetanus) 7 day proliferation (CFSE dye dilution by flow cytometry)/cytokine secreting (supernatant analysis for Th1 and Th2 and Th17 cytokines by luminex) assays in the presence of IL2 supplementation, and presence vs. absence of ENPP2 inhibitor (100 nM PF8380, Pfizer, recently obtained via MTA with Pfizer, PD1 blockade (10 ug/ml anti-PDL1, eBioscience) or Tim3 blockade (10 ug/ml anti Tim3 Biolegend) as previously described. We will also perform bulk T cell stimulation via anti-CD3 and anti-CD28 agonistic antibodies, performed in presence vs. absence of the above blocking reagents.

Figure 2:
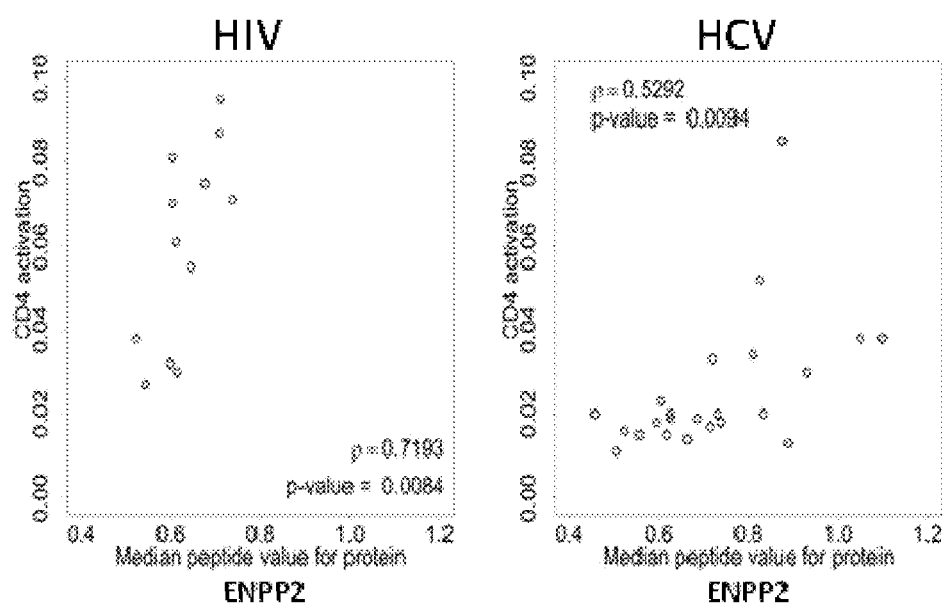
FIG. 2 illustrates plasma proteome analysis revealing ENPP2 as positively correlating with CD4 cell activation in HCV and HIV infected subjects. Plasma proteome peptide intensity vs. CD4 cell activation (proportion of CD4 cells expressing HLADR and CD38, determined by flow cytometry) is plotted for HIV infected subjects off HIV therapy (n=12) and for untreated chronic HCV infected subjects (n=24, HCVlo and HCVhi combined). Similar results were observed comparing ENPP2 level determined by ELISA method with T cell activation (not shown).

Sub Aim C/D: IL-6, sCD14, and T cell activation will be measured as shown in FIG. 1. Sub Aim D: Immunogen specific serum antibody titer will be measured by ELISA.

Anticipated outcome. Aim 1A: We anticipate LPA mediated CD4 activation will occur with isolated CD4 cells because LPA receptors are present on CD4 cells, though enhanced by the presence of accessory cells. For CD8 cell activation we anticipate accessory cell activity is required because LPA receptors are not present on CD8 cells. Similarly, LPA receptors exist on DC, monocyte/macrophages, and B cells, so we anticipate LPA to induce activation of these populations as well, some requiring accessory cell activity for maximal activation. Aim 1B: We anticipate ENPP2 blockade will enhance memory proliferative and cytokine secreting responses to HBV/HAV antigen more so than tetanus, and that enhancement will compare in magnitude to Tim3 and PD1 blockade. These results would implicate ENPP2 and LPA as another inhibitory pathway amenable to interruption. Aim 1C. We anticipate ENPP2 and soluble and cellular markers of immune activation will normalize in low APRI (low liver damage) subjects after sustained response to therapy, while it will not normalize in high APRI (high liver damage) subjects. Aim 1D: We anticipate that during HCV infection there is an impaired response to neoantigen (HBV/HAV), but not recall antigen (tetanus toxoid). We anticipate immune activation parameters and ENPP2 level will negatively predict vaccine response.

Aim 2:

To determine the effect of ENPP2 inhibition on murine host response to neoantigen in the setting of chronic LCMV infection. We have identified lead markers of dysfunctional immune activation in persistent viral infection. The best way to test physiological significance is via blockade during a naturally persistent viral infection. Small animal models provide the most feasible and tractable approach. The most extensive experience for such studies is with the LCMV system. Study of LCMV has established more generalizable rules of viral immunology than any other system. Moreover high level RNA viremia established during persistent LCMV infection results in immune activation leading to immune dysfunction, loss of naïve CD4 T cells and induction of ENPP2 (FIG. 7) during this infection which seeds the liver and results in transaminitis. Because of the many parallels with HCV & HIV, as well as being the best characterized model for chronic viral infection, we propose this is the best system to investigate ENPP2 effects on neoantigen response and ongoing infectious viral replication.

Figure 8:
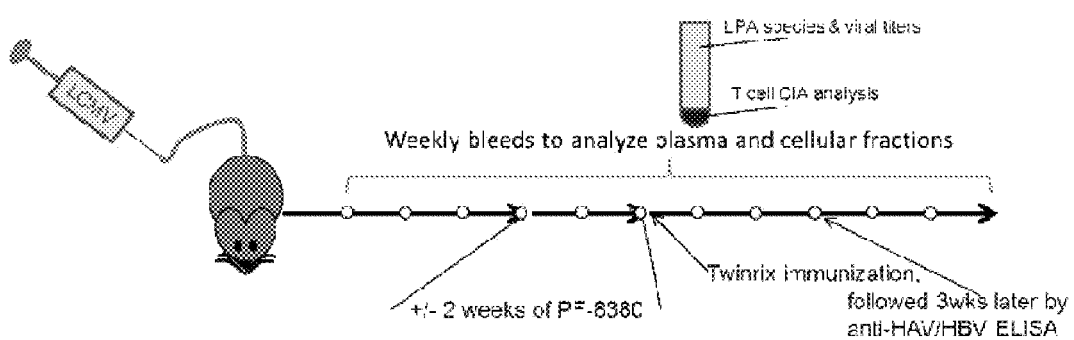
FIG. 8 illustrates that 5-6 wk old adult mice will be persistently infected with LCMV Clone13 and immune responses and control of viremia will be determined. ENPP2 activity will be inhibited between weeks 4 and 6 post infection, p.i. (each white dot representing 1 week of time p.i.). The affect of ENPP2 activity on viremia and LCMV specific-T cell numbers and cytokine responses from peripheral blood collections by MHC tetramer analysis and ex vivo peptide stimulation, respectively, is determined by sampling peripheral blood at weekly timepoints. Parallel, Twinrix will be given to determine neoantigen responses, with antibody responses quantitated by ELISA. Animals will be harvested at key timepoints based on initial findings in the peripheral blood to determine viral loads, ENPP2 levels and T cell responses in key organs (i.e., liver and secondary lymphoid tissue).

We will determine LPA levels and effect of ENPP2 blockade on viral titers, cognate immune responses and neoantigen response during persistent viral infection in mice. Based upon our model we hypothesize that sustained induction of ENPP2 and its pro-inflammatory lipid mediator LPA results in dysfunctional neoantigen responses and deleterious effects on control of viral loads. We believe these effects will be reversed with ENPP2 inhibition. Here we will inhibit ENPP2 function using a human/murine active ENPP2 inhibitor PF-8380 we have obtained from Pfizer. We will establish a persistent LCMV Cl13 infection in C57BL/6 mice 6-8 weeks of age (5 mice/group×3 experiments) and collect peripheral blood at weekly time points post-infection (experimental outline is graphically illustrated in FIG. 8). ENPP2 inhibition will be accomplished by treating with PF-8380 bid×2 weeks at 30 mg/kg as described four weeks after establishment of infection. We will assess T cell activity (2 wk after PF-8380 treatment) and viremia as these are the two most critical physiological endpoints in both mouse and human for effective anti-viral immunity versus dysfunctional CIA. Lastly, we propose to immunize mice with Twinrix 4 weeks after viral infection and assess antibody responses.

Our experimental groups are as follows: (1) LCMV Cl13 ENPP inhibition vs. (2) vehicle control to assess T cell responses and viral titers from peripheral blood; (3) same as "1" looking at Twinrix response vs. (4) same as "2" looking at Twinrix response. The sample size will yield adequate statistical power in our experience given that we are looking for >1 log differences between key groups regarding infectious viral titers. In addition, our experience with LCMV has been that the standard deviation for each sample (e.g., viral loads and LCMV-specific T cell numbers and cytokine production) was <20% of the sample average value for each sample within an experimental group of sample size=5. Taken together, this power analysis predicts that we will have an alpha error level of <5% or confidence level >95% for probability of incorrectly rejecting the null hypothesis.

These samples will be analyzed for ENPP2 and LPA as described in Aim 1 (for LPA) and FIG. 7. Based on these results from plasma, a subset of time points will be chosen to harvest organs from a subsequent group (n=5) of mice to identify the primary source of ENPP2 during persistent viral infection. Additionally, the cellular fraction of collected samples will be used 9 dpi during the peak T cell response against LCMV, to access T cell function. LCMV antigen specific T cells will be enumerated with tetramers and cytokine production (IL-2, IFNg and TNFa) measured in ex vivo peptide restimulation assays as published previously. Additionally, plasma from all time points will be used to titer infectious virus.

Based upon our preliminary data (FIG. 7) we expect that induction of ENPP2 and LPA will occur in persistently infected mice. We predict that the source of ENPP2 will be primarily hepatic. We suspect that this pathway will deleteriously contribute to T cell function and neoantigen response, which will be at least partially reversed with PF-8380 treatment. As an additional product of our LCMV-specific tetramer and peptide restimulation analysis, we will also measure bystander viral antigen independent T cell numbers and function which may play a role in neoantigen responses. Response to LCMV itself is also anticipated to be affected by ENPP2 inhibition. Our preliminary data indicate ENPP2 levels vary by infection outcome in this system, and if our model holds we will be able to formally prove causality by using the ENPP2 inhibitor PF-8380 systemically after viral infection is established.

I claim:

1. A method of determining the risk of cardiovascular disease in a subject having a chronic viral infection, the method comprising:

obtaining a biological sample from the subject;
determining a level of ectonucleotide pyrophosphatase/phosphodiesterase-2 (ENPP2) in the biological sample wherein the level of ENPP2 is determined using an ELISA assay;
determining whether the subject has an increased risk of cardiovascular disease associated with the chronic viral infection by comparing the determined level of ENPP2 to a control level, the control level comprising the level of ENPP2 in a population of subjects having a chronic viral infection but not having cardiovascular disease associated with the chronic viral infection, wherein an increased level of ENPP2 is indicative of the subject having an increased risk of cardiovascular disease associated with the chronic viral infection and resulting from chronic immune activation (CIA) mediated by the chronic viral infection; and
administering a therapeutically effective amount of an ENPP2 inhibitor to the subject, the subject having increased levels of ENPP2 as compared to the control level, wherein the ENPP2 inhibitor is selected from the group consisting of Brp-LPA, PF8380, S 32826, HA 130 and ONO-8430506.

2. The method of claim 1, wherein the one or more biological samples comprises blood serum or plasma.

3. The method of claim 1, wherein the cardiovascular disease is selected from the group consisting of myocardial infarction, coronary artery disease, angina, atherosclerosis, aneurysm, congestive heart failure, left ventricular dysfunction, and cerebrovascular disease.

4. The method of claim 1, wherein the chronic viral infection is selected from the group consisting of HIV (human immunodeficiency virus), HCV (hepatitis C virus) and HIV/HCV co-infection.

* * * * *